United States Patent [19]

Going

[11] Patent Number: 5,064,830
[45] Date of Patent: Nov. 12, 1991

[54] LOWERING OF BLOOD URIC ACID LEVELS

[75] Inventor: Paden C. Going, Preston, Conn.

[73] Assignee: Pfizer Inc., New York, N.Y.

[21] Appl. No.: 562,096

[22] Filed: Aug. 2, 1990

[51] Int. Cl.$^5$ .................... A61K 31/38; A61K 31/50; A61K 31/425; A61K 31/495
[52] U.S. Cl. .................................... 514/252; 514/367; 514/444
[58] Field of Search ..................... 514/252, 367, 444

[56] References Cited

U.S. PATENT DOCUMENTS 4,939,140  7/1990  Larson et al. .................. 514/222

FOREIGN PATENT DOCUMENTS 222576   5/1987  European Pat. Off. .
2201343  9/1988  United Kingdom .

OTHER PUBLICATIONS

Cited to Show State of the Art.

*Primary Examiner*—Stanley J. Friedman
*Attorney, Agent, or Firm*—Peter C. Richardson; Paul H. Ginsburg; Gezina Holtrust

[57] ABSTRACT

Certain derivatives of oxophthalazinyl acetic acids of the formula

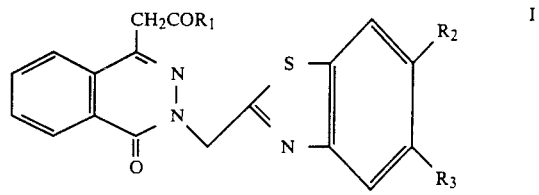

wherein $R_1$ is hydroxy or a prodrug group, and $R_2$ and $R_3$ are independently hydrogen, fluoro, chloro or trifluoromethyl, except that $R_2$ and $R_3$ are not both hydrogen, or a pharmaceutically acceptable base addition salt of a compound of formula I wherein $R_1$ is hydroxy, are capable of lowering blood uric acid levels in mammals. These oxophthalazinyl acetic acid derivatives are for instance useful for treating gout and gouty arthritis in a mammal.

2 Claims, No Drawings

LOWERING OF BLOOD URIC ACID LEVELS

BACKGROUND OF THE INVENTION

This invention relates to a method of lowering blood uric acid levels in a mammal by use of certain derivatives of benzothiazolyl oxophthalazinyl acetic acid.

Benzothiazolyl oxophthalazinyl acetic acids are disclosed in European patent publication 222,576 for use in the treatment of chronic complications arising from diabetes mellitus. The use of these benzothiazolyl oxophthalazinyl acetic acids for lowering blood uric acid levels in mammals and for treatment of gouty arthritis in mammals is not disclosed.

U.K. patent publication 2,201,343 refers to the use of 3-(4-bromo-2-fluorophenyl)-4-oxo-3H-phthalazin-1-ylacetic acid in lowering blood uric acid levels. The reference discloses many diseases in which lowered blood uric acid levels occur such as gout, gouty arthritis, pneumonia, certain blood diseases such as myeloid leukemia and pernicious anemia, and renal diseases. The reference does not disclose the use of the present derivatives of benzothiazolyl oxophthalazinyl acetic acid.

SUMMARY OF THE INVENTION

According to the invention, a benzothiazolyl oxophthalazinyl acetic acid of the formula

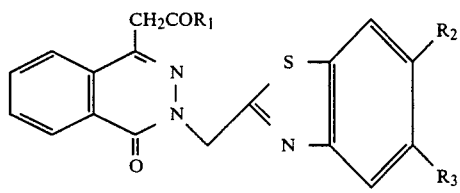

wherein $R_1$ is hydroxy or a prodrug group, and $R_2$ and $R_3$ are independently hydrogen, fluoro, chloro or trifluoromethyl, except that $R_2$ and $R_3$ are not both hydrogen, and the pharmaceutically acceptable base addition salts thereof when $R_1$ is hydroxy lower blood uric acid levels in mammals, and therefore are useful in the treatment of gouty arthritis and other diseases in mammals.

The preferred methods use the compound of formula I wherein R is hydroxy, $R_2$ is hydrogen and $R_3$ is trifluoromethyl: 3-(5-trifluoromethylbenzothiazol-2-ylmethyl)-4-oxo-3-H-phthalazin-1-ylacetic acid.

The methods of using a compound of formula I or its pharmaceutically acceptable base addition salt (the active compound) comprise administering to a mammal an effective amount of such compound. Administration comprises any known method for therapeutically providing an active compound to a mammal such as by oral or parenteral administration.

DETAILED DESCRIPTION OF THE INVENTION

The active compounds and their preparation are disclosed in European patent publication 222,576.

As disclosed in European patent publication 222,576, the term "prodrug" group denotes a group that is converted in vivo into a hydroxy group. Groups that may be used to form prodrugs are generally known in the art and include ester forming groups to form an ester prodrug. Examples of prodrug groups are benzyloxy, di(C$_1$-C$_4$)alkylaminoethyloxy, acetoxymethyl, pivaloyloxymethyl, phthalidoyl, ethoxycarbonyloxyethyl, 5-methyl-2-oxo-1,3-dioxol-4-ylmethyl, (C$_1$-C$_4$)-alkoxy optionally substituted by N-morpholino, and amideforming groups such as di(C$_1$-C$_4$)alkylamino.

As disclosed in European patent publication 222,576, the active compounds will form pharmaceutically acceptable base addition salts. All such salts are within the scope of this invention and can be prepared as described in European patent publication 222,576. Examples of suitable cations to form the base addition salts are alkali metal cations such as potassium and sodium, and alkaline earth metal cations such as calcium and magnesium. Suitable base addition salts further may be formed by reaction of a compound of formula I wherein $R_1$ is hydroxy with ammonium, water-soluble amines such as N-methylglucamine (meglumine), a (C$_1$-C$_4$)alkanol ammonium or other organic amines which are pharmaceutically acceptable. In general, the sodium and N-methylglucamine salts are preferred.

The active compounds may be used for treatment of gout or gouty arthritis and other diseases in which lowered blood uric acid levels occur, e.g. those mentioned above. As used in the claims and specification hereof, treatment is meant to include both the prevention and alleviation of arthritis and other diseases.

The active compound may be administered to a subject in need of treatment by a variety of conventional routes of administration, including orally, parenterally and topically. In general, the active compound will be administered orally or parenterally at dosages between about 0.5 and 25 mg/kg body weight of the subject to be treated per day, preferably from about 1.0 to 10 mg/kg. However, some variation in dosage will necessarily occur depending on the condition of the subject being treated. The person responsible for administration will, in any event, determine the appropriate dose for the individual subject.

The active compound may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the active compound and the pharmaceutically acceptable carriers are then readily administered in a variety of dosage forms such as tablets, powders lozenges, syrups, injectable solutions and the like.

These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerine and combinations thereof.

For parenteral administration, solutions of the active compound in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques.

The ability of the active compound to lower blood uric acid levels is demonstrated as follows. A urine sample of a mammal such as a human is mixed with the enzyme uricase, a uric acid reagent and a uric acid diluent. The uric acid reagent contains nicotinamide adenine dinucleotide phosphate (NADP), the enzyme catalase and aldehyde dehydrogenase. The uric acid diluent consists of ethanol, glycerol and potassium chloride. The uricase is added to the uric acid reagent and the mixture is combined with the remaining ingredients. The final mixture is photometrically monitored by observation of an increase in the absorbance at 340 nm as NADPH is formed from NADP. The increase is directly proportional to the uric acid content of the original sample since in the overall reaction one micromole of NADPH is produced for each micromole of uric acid in the original sample.

I claim:

1. A method of lowering blood uric acid levels in a mammal in need of such lower levels which comprises administering to said mammal a blood uric acid level lowering amount of a compound of the formula

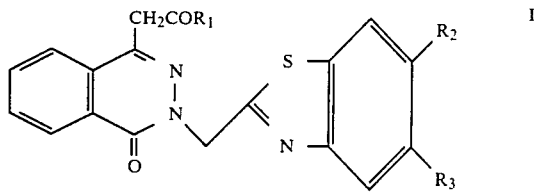

wherein $R_1$ is hydroxy or a prodrug group, and $R_2$ and $R_3$ are independently hydrogen, fluoro, chloro or trifluoromethyl except that $R_2$ and $R_3$ are not both hydrogen, or a pharmaceutically acceptable base addition salt of a compound of formula I wherein $R_1$ is hydroxy.

2. A method according to claim 1 wherein $R_2$ is hydrogen and $R_3$ is trifluoromethyl.

* * * * *